United States Patent
Say (10) Patent No.: US 7,063,688 B2
(45) Date of Patent: Jun. 20, 2006

(54) PORTABLE BATTERY OPERATED ASPIRATOR

(75) Inventor: Samuel L. Say, La Cañada, CA (US)

(73) Assignee: Say Family Trust, La Canada, CA (US)

( * ) Notice: Subject to any disclaimer, the term of this patent is extended or adjusted under 35 U.S.C. 154(b) by 238 days.

(21) Appl. No.: 10/376,496

(22) Filed: Feb. 28, 2003

(65) Prior Publication Data

US 2003/0163101 A1    Aug. 28, 2003

Related U.S. Application Data

(60) Provisional application No. 60/360,289, filed on Feb. 28, 2002.

(51) Int. Cl.
    *A61M 1/00* (2006.01)

(52) U.S. Cl. .................................. 604/319; 604/118

(58) Field of Classification Search ............... 604/131, 604/27, 30, 35, 36, 37, 38, 118, 317–319, 604/320–328, 313; 137/205; 128/205.12, 128/205.19
    See application file for complete search history.

(56) References Cited

U.S. PATENT DOCUMENTS

| | | | | |
|---|---|---|---|---|
| 4,643,719 A | * | 2/1987 | Garth et al. | 604/73 |
| 4,747,166 A | | 5/1988 | Kuntz | |
| 4,747,844 A | * | 5/1988 | Elliott | 604/319 |
| 4,930,997 A | * | 6/1990 | Bennett | 417/410.1 |
| 4,998,915 A | * | 3/1991 | Hannah | 604/73 |
| D327,342 S | * | 6/1992 | Leung | D32/18 |
| 5,134,994 A | * | 8/1992 | Say | 128/200.24 |
| 5,466,229 A | * | 11/1995 | Elson et al. | 604/317 |
| 5,662,627 A | | 9/1997 | Say | |
| 5,800,425 A | * | 9/1998 | DeLeonardis | 604/27 |
| 6,059,803 A | * | 5/2000 | Spilman | 606/162 |
| 6,648,862 B1 | * | 11/2003 | Watson | 604/319 |

OTHER PUBLICATIONS

Dick, Thom, "SSCOR Introduces Compact New Suction", SSCOR, Inc. advertisement (reprinted from Emergency Medical Services Magazine, Oct. 2004), 1 page.

Pridemark Paramedic Services, L.L.C. advertisement entitled "Your Suction Device is . . . Different.", 1 page.

SSCOR, INC. operating instructions entitled "Your S-SCORT . . . Jr. Quickdraw Suction Device is Different!!!—To Operate Your Quickdraw Suction Unit . . . ", 2 pages.

(Continued)

*Primary Examiner*—Nicholas D. Lucchesi
*Assistant Examiner*—Matthew F. DeSanto
(74) *Attorney, Agent, or Firm*—Christie, Parker & Hale, LLP (57) ABSTRACT

A portable aspirator has a canister, a housing that removably receives the canister, and a rigid catheter directly connected to the canister. Preferably, the canister and the catheter are molded or otherwise formed in a one piece construction. An inlet port on the housing and an outlet chamber from the canister are provided with seals to form an air tight connection between the housing and the canister. The canister is constructed to form a labyrinthine path from the catheter to the outlet chamber.

19 Claims, 7 Drawing Sheets

OTHER PUBLICATIONS

Product brochure entitled "Experience real freedom—Clario Home Care Pump", 2 pages.

Internet: http://www.medela.ch/ism/news_7.html (Medela-News), 3 pages.

* cited by examiner

PORTABLE BATTERY OPERATED ASPIRATOR

CROSS-REFERENCE TO RELATED APPLICATION

This application claims priority of U.S. Provisional Application No. 60/360,289, filed Feb. 28, 2002, the disclosure of which is incorporated frilly herein by reference.

BACKGROUND OF THE INVENTION

This invention relates to emergency medical equipment, and more particularly, to a portable battery operated aspirator.

Aspirators are used in an emergency medical setting, usually at the site of a medical emergency or in a hospital, to clear obstructions, namely fluids and debris, from the airway of a patient. Light weight, ease of handling, dependability, exceptional performance, and durability are useful characteristics for this purpose.

SUMMARY OF THE INVENTION

According to the invention, a portable aspirator has a canister, a housing that removably receives the canister, and a catheter directly connected to the canister. Preferably, the canister and the catheter are molded or otherwise formed in a one piece construction. An inlet port that extends from the housing and an outlet chamber in the canister are provided with seals to form an air tight connection between the housing and the canister. The canister is constructed to form a labyrinthine path from the catheter to the outlet chamber.

BRIEF DESCRIPTION OF THE DRAWINGS

The features of a specific embodiment of the best mode contemplated of carrying out the invention is illustrated in the drawings, in which.

DETAILED DESCRIPTION OF THE SPECIFIC EMBODIMENT

Figure 2:
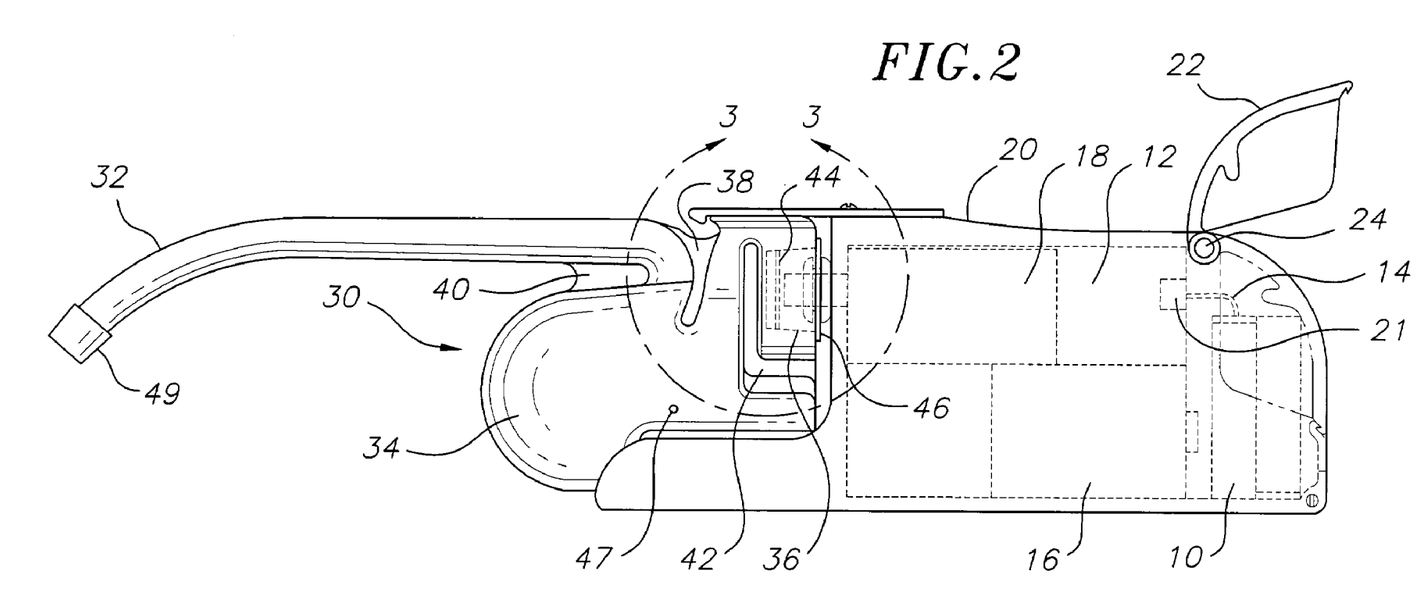
FIG. 2 is a side elevation view of the canister of FIG. 1 installed in the housing of FIG. 1.
Figures 4, 5:
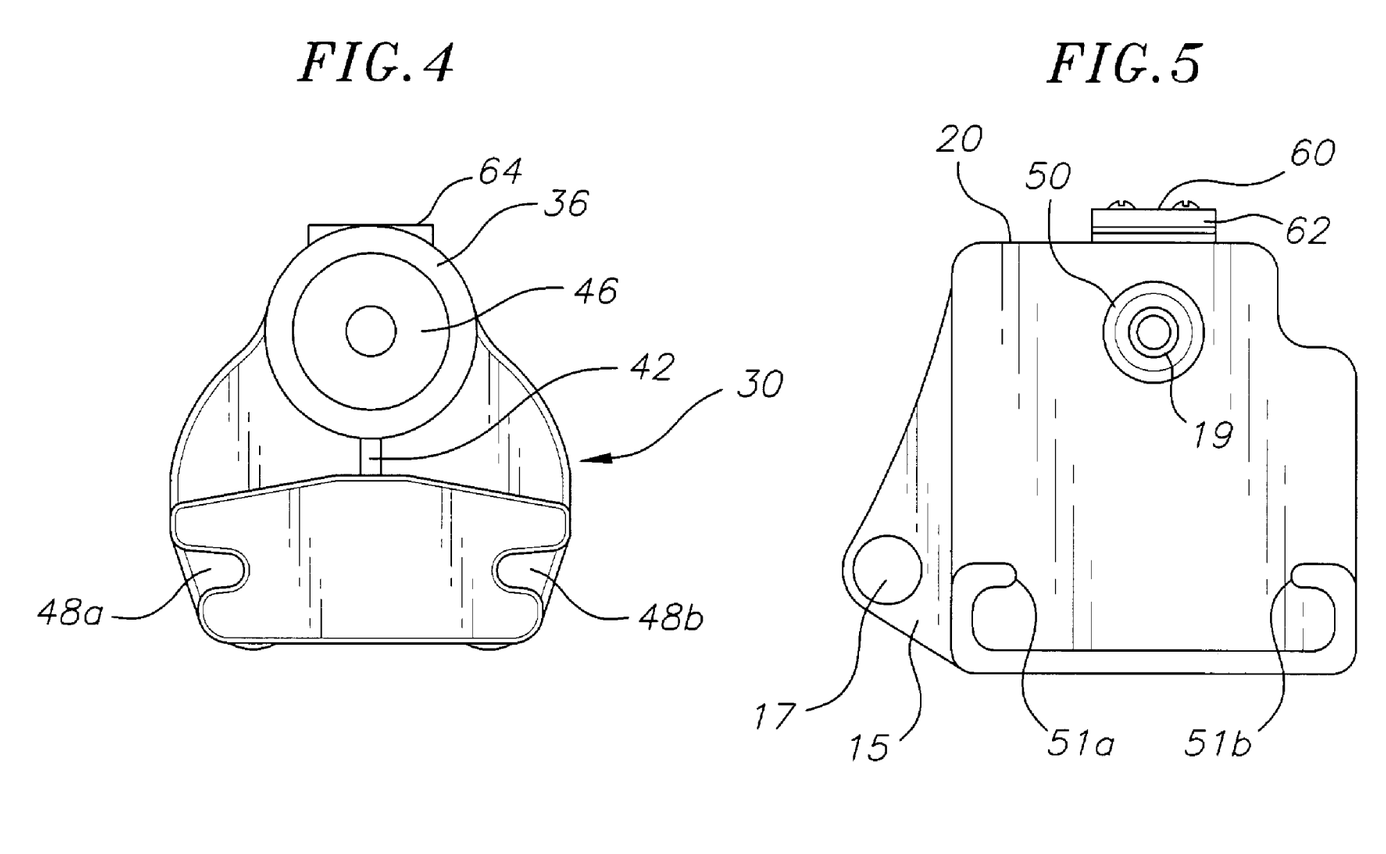
FIG. 4 is an end view of the canister of FIG. 1 taken in the direction of the arrows on the plane 4—4 in FIG. 1.
FIG. 5 is an end view of the housing of FIG. 1 taken in the direction of the arrows on the plane 5—5 in FIG. 1.
Figure 7:
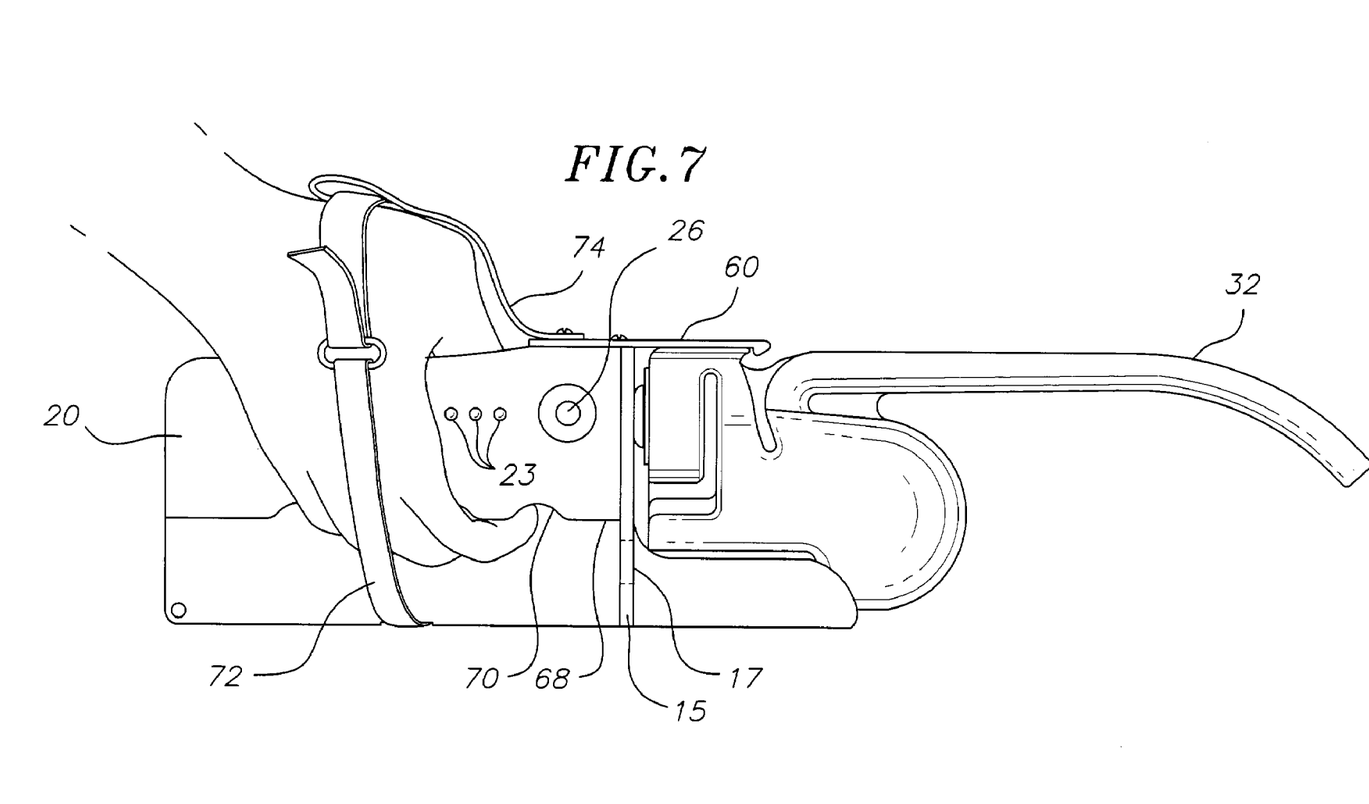
FIG. 7 is a side elevation view of the housing and canister of FIG. 2 with carrying straps illustrating how the aspirator may be gripped in use.
Figure 8:
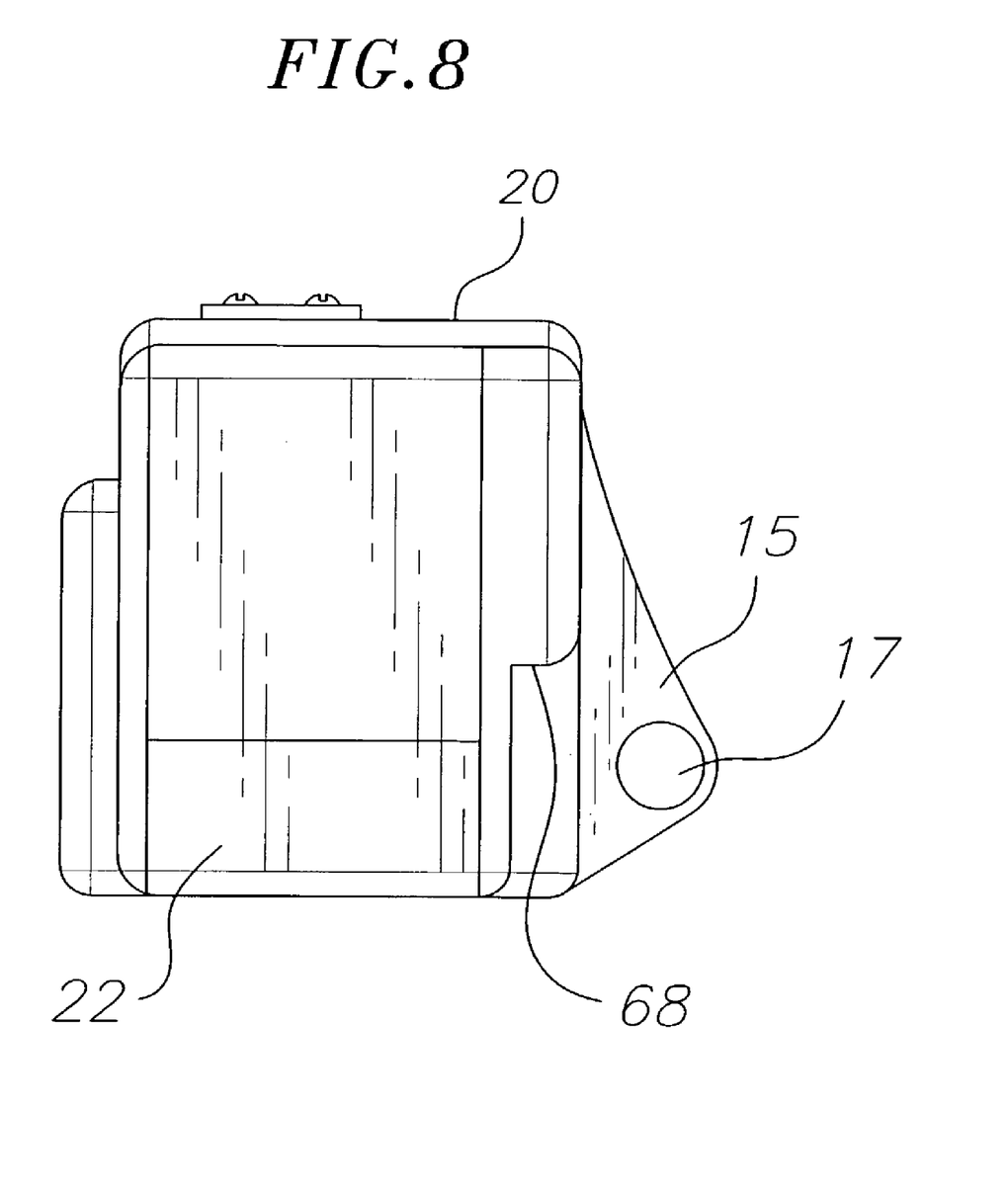
FIG. 8 is a front elevation view of the housing and canister of FIG. 2 with the outboard catheter holder cut away to show the finger gripping surface of the PC Board holder along the side of the housing.

With reference to FIG. 2 a battery 10, a circuit board 12, a cable 14, an electric motor 16, and a vacuum pump 18 are disposed in a housing 20. Battery 10 is electrically connected to a right angle jack 21 by cable 14. Jack 21 plugs into a receptacle mounted on circuit board 12 to furnish power thereto. From circuit board 12 power is delivered to motor 16, which drives pump 18. Electronics for performing various functions such as battery charging and status display are mounted on circuit board 12. Battery 10 is charged through an external receptacle (not shown) and jack 21. Status lamps 23 are displayed through housing 20 (FIG. 7). An outboard catheter holder 15 with a hole 17 is formed in the side of housing 20 (FIG. 5). An intake port 19 of the pump 18 protrudes through housing 20. An access door 22 at the back of housing 20 has a hinge 24. The unhinged end of door 22 is designed to form a snap fit with housing 20. To replace battery 10, door 22 is swung open as shown in FIG. 2 and cable 14 is disconnected. A start button 26 (FIG. 7) that is accessible from the exterior of housing 20 turns motor 16 on and off.

Figure 1:
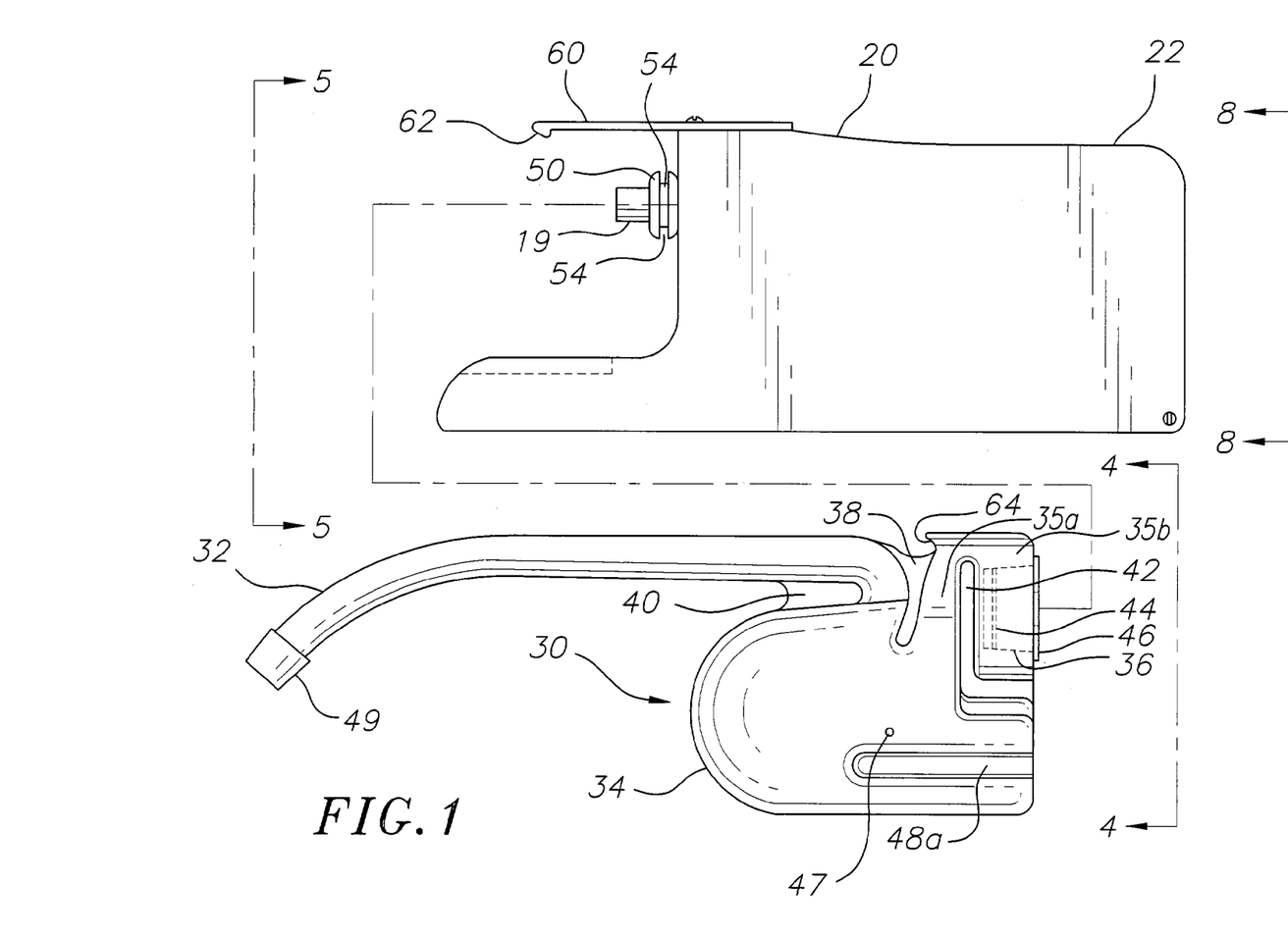
FIG. 1 is a side elevation view of an aspirator housing and a removable canister incorporating principles of the invention; the canister is removed from the housing.

With particular reference to FIG. 2, a disposable canister 30 is preferably molded or vacuformed from clear nonreactive plastic, such as polypropylene. A catheter 32, which has a downwardly curved anatomically correct shape for insertion in the throat of a human patient, is directly connected to canister. (Catheter 32 is preferably rigid.) As a result, there is little flow resistance between the catheter and canister, which permits the use of a small motor and pump. Preferably, catheter 32 is molded with canister 30 in a one piece construction. Alternatively, however, catheter 32 could be formed as a separate part that is coupled to canister 30 by, for example, a threaded or bayonet connection. Catheter 32 is rigid. Catheter 32 feeds a collection chamber 34 in canister 30, which leads to a slightly conical outlet chamber 36, Webs 38,40 and 42 are formed in the molding process. Web 38 forms a goose neck-like path between catheter 32 and collection chamber 34 and web 42 forms a tortuous path from collection chamber 34 to outlet chamber 36. Outlet chamber 36 is made from an elastomeric material. A circular filter 44 is mounted in outlet chamber 36, for example by a groove that captures the edge of filter 44, and an annular elastomeric sealing washer 46 extends around the exit from outlet chamber 36 (FIG.1). Filter 44 is a porous hydrophobic disk coated with a material that blocks the pores when exposed to water. An exemplary filter for this purpose is Porex part no. X-5422. An elastomeric grommet 50 is mounted on intake port 19 (FIG. 1). A groove 54, is formed around the periphery of grommet 50.

Figure 3:
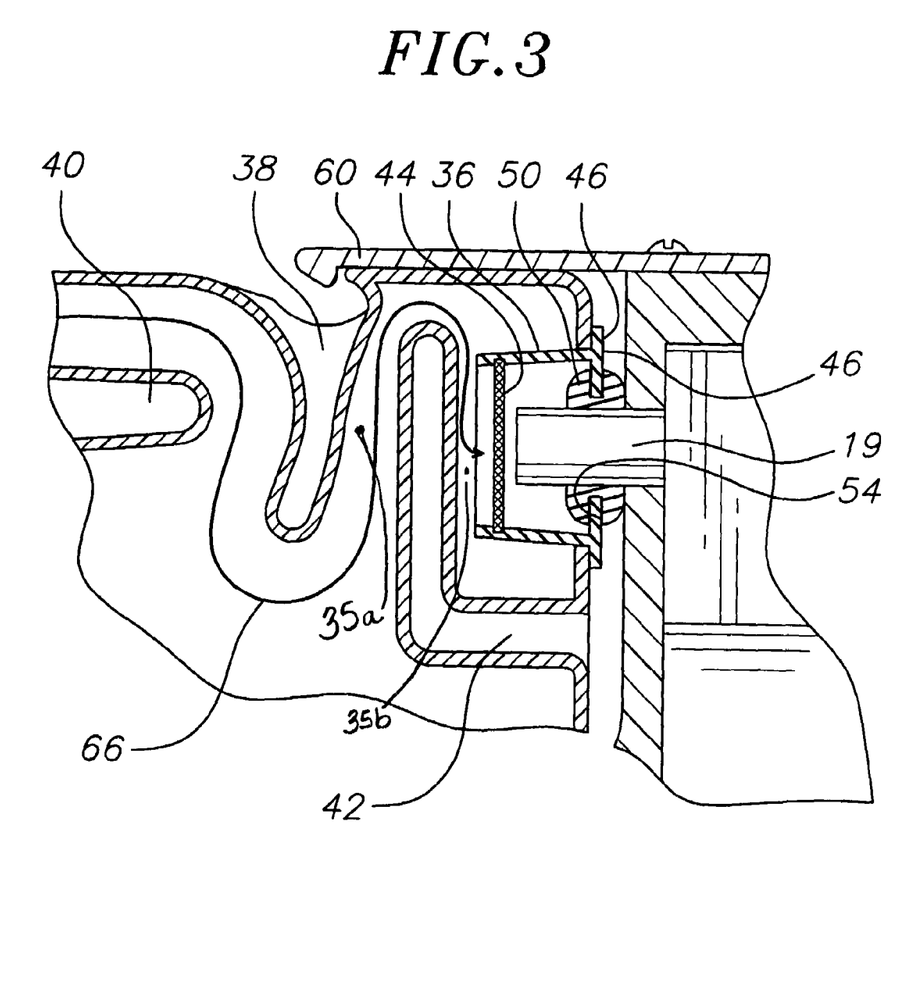
FIG. 3 is an enlarged view of the interface between the housing and canister of FIG. 2.

To install canister 34 on housing 20, side grooves 48a, 48b on canister 30 (FIG. 4) slide on rails 51a,51b toward housing 20 so sealing washer 46 is aligned with intake port 19 until sealing washer 46 abuts and compresses grommet 50 to insure an air and liquid tight connection to housing 20. As shown in FIG. 3, the inner edge of washer 46 fits in groove 54 and is thus captured by grommet 50. Grommet 50, which abuts the front surface of housing 20, serves as a stop on the movement of canister 30 during installation. As a result, seals 46 and 50 are both somewhat compressed, which insures that no leakage takes place at the interface of canister 30 and housing 20. A resilient clamp 60 mounted on housing 20 has a downwardly facing hook 62 that snaps against a lip 64 on the top of canister 30 as canister 30 is installed. Clamp 60 holds canister 30 against housing 20 so washer 46 and grommet 50 remain compressed. To disengage canister 30 from housing 20, clamp 60 is pushed upwardly, which releases hook 62 from lip 64.

When the aspirator is turned on by start button 26, suction is developed at the end of catheter 32. Consequently, air and entrained bodily fluids are drawn through catheter 32 into collection chamber 34. As shown by a line 66(FIG. 3), the air follows a labyrinthine path 35a and 35b from catheter 32 to outlet chamber 36, but the fluids are by in large deposited in chamber 34. The air and entrained fluids are first drawn downwardly due to the baffle formed by web 38, where much of the fluid is separated from the air. The air then flows up and around the baffle formed by web 42 and into filter 44. There is a narrow space between the baffle formed by web 42 and the end of outlet chamber 36 restricting the access of fluids to the surface of filter 44. In addition, any fluids that reach the surface of filter 44 are prevented from entering intake 19 because of the characteristics of filter 44 described above. In summary, the labyrinthine path 66 separates, to a large degree, the bodily fluids from the airflow, and thus reduces the exposure of the filter element 44 to the bodily fluids, and filter 44 provides further assurance that pump 18 remains free of such fluids. A removable plug 47 covers a hole in canister 30 (not shown). To reduce the suction of the aspirator, plug 47 is removed so the vacuum in canister drops. A removable cap 49 is stored on the side of canister 30 when the aspirator is turned on. After the aspirator is turned off, cap 49 is placed on the end of catheter 32 to prevent escape of fluids from canister 30.

For a right-handed user, the right side of housing 20 has a longitudinal shelf 68 with finger grips 70 along its edge. A strap 72 extends loosely enough around housing 20 for insertion of a user's hand. Strap 72 has a cross-strap 74 which is secured to clamp 60. FIG. 7 illustrates how the user may hold the aspirator in use.

Figure 6:
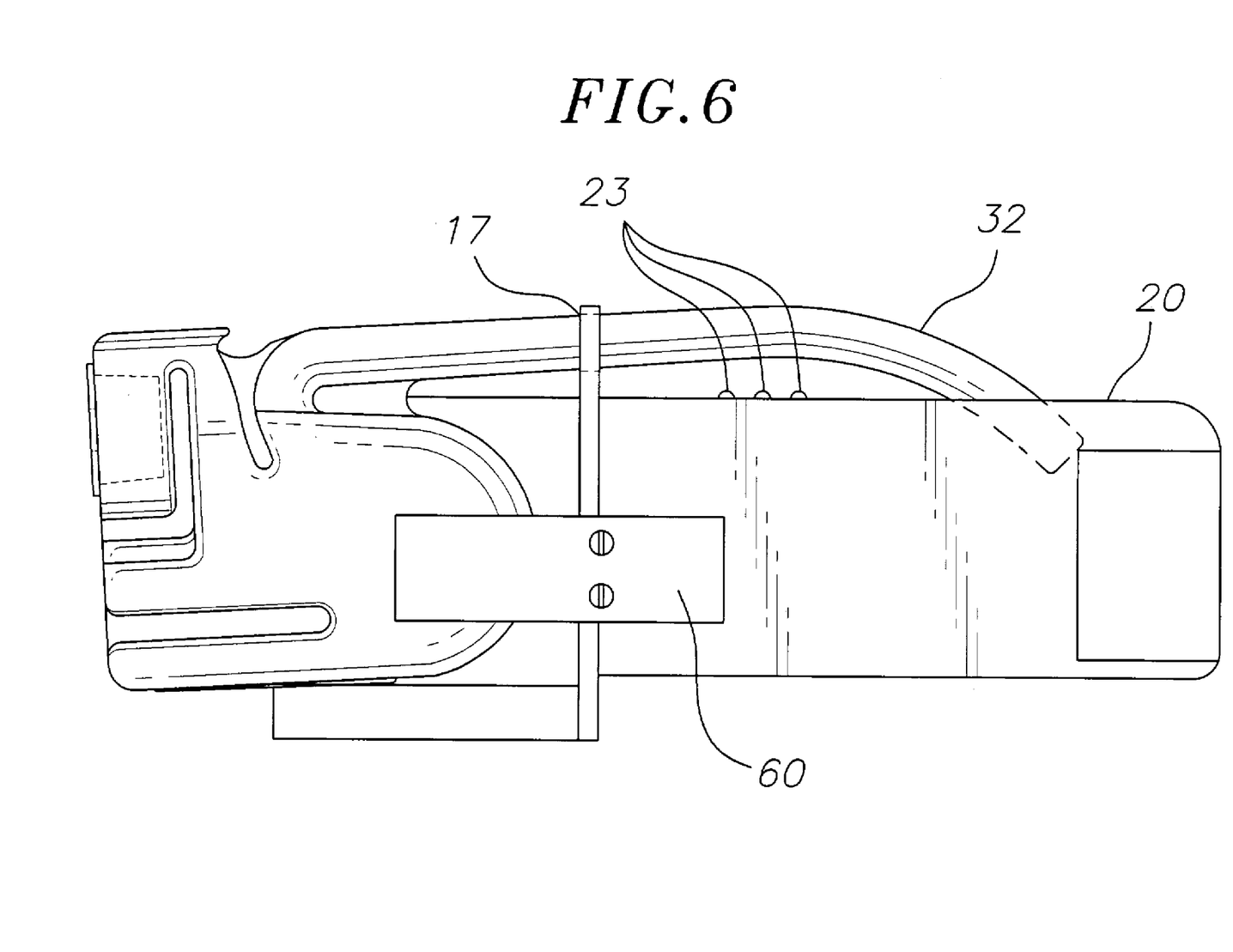
FIG. 6 is a top elevation view of the housing and canister of FIG. 2 positioned for shipment or storage when the aspirator is out of use.

To store or transport the described aspirator, canister 30 is turned around so catheter 32 faces housing 20, is turned 90 degrees from its installed orientation, and pushed into hole 17 in holder 15. As illustrated in FIG. 6, the resulting configuration is compact and suitable for shipping to customers and storage.

The described embodiment of the invention is only considered to be preferred and illustrative of the inventive concept; the scope of the invention is not to be restricted to such embodiment. Various and numerous other arrangements may be devised by one skilled in the art without departing from the spirit and scope of this invention.

What is claimed is:

1. A portable handheld aspirator comprising:
   a housing having an intake port;
   a battery operated vacuum pump in the housing for creating suction at the intake port;
   a fluid storage canister removably received by the housing and connected to the intake port of the housing;
   a catheter directly connected to the canister, the catheter having an inlet and a passage from its inlet to the canister that results in little flow resistance
   the catheter being rigid from its inlet to the housing, and
   the canister connected to the catheter and intake port of the housing, wherein the canister includes a labyrinthine path that separates bodily fluid from airflow.

2. The aspirator of claim 1, in which the canister has an exit and an annular seal that surrounds the exit to form an air tight connection to the intake port of the housing.

3. The aspirator of claim 2, in which a grommet is mounted on the intake port of the pump and the grommet has a groove that compresses to form the air tight connection.

4. The aspirator of claim 3, in which the grommet and the seal are compressed when the housing receives the canister.

5. The aspirator of claim 4, in which the grommet and the seal are compressed by a clamp that releasably connects the canister to the housing.

6. The aspirator of claim 1, additionally having a porous hydrophobic filter between the canister and the intake port, the filter having pores that are blocked when exposed to water.

7. The aspirator of claim 6, in which the filter and the canister are formed to define an annular chamber around the filter.

8. The aspirator of claim 7, in which the catheter is connected to the canister near the top of the canister and the canister is connected to the intake port near the top of the canister.

9. The aspirator of claim 6, in which the filter extends into the canister and the canister has a baffle spaced closely from the filter to block fluid flow into the filter.

10. The aspirator of claim 1, in which the canister is constructed so the canister has a collection chamber near the bottom of the canister, the catheter is near the top of the front of the canister, and the exit is near the top of the back of the canister.

11. The aspirator of claim 10, in which the canister is constructed to form a rear baffle between the collection chamber and the exit.

12. The aspirator of claim 11, in which the canister is constructed to form a front baffle that deflects air entering the canister from the catheter toward the bottom of the collection chamber.

13. The aspirator of claim 1, in which the catheter has a downwardly curved anatomically correct shape for insertion in the throat of a human patient.

14. The aspirator of claim 13 in which the canister and the catheter are formed in a one piece construction.

15. The aspirator of claim 1, additionally comprising a motor that drives the pump, and wherein the housing had a door for access to the battery for replacement.

16. The aspirator of claim 1, in which one of the canister and the housing has a pair of rails and the other of the canister and the housing has a pair of grooves that removably receives the canister.

17. The aspirator of claim 1, additionally comprising a seal between intake port and the canister.

18. The aspirator of claim 1, in which the catheter and the canister are formed as a single part.

19. The aspirator of claim 1, in which the labyrinthine flow entering the canister at the catheter first flows downwardly and then flows upwardly before reaching the annular chamber.

* * * * *